United States Patent [19]

Epperson et al.

[11] Patent Number: 5,808,151
[45] Date of Patent: Sep. 15, 1998

[54] BIPHENYLAMIDO DERIVATIVES AS MELATONERGIC AGENTS

[75] Inventors: James R. Epperson, Cromwell; Joseph P. Yevich, Southington, both of Conn.

[73] Assignee: Bristol-Myers Squibb Company, Princeton, N.J.

[21] Appl. No.: 835,456

[22] Filed: Apr. 8, 1997

Related U.S. Application Data

[60] Provisional application No. 60/015,797, Apr. 17, 1996.

[51] Int. Cl.$^6$ ............... C07C 233/07; C07C 233/18; C07C 233/20; A61K 31/165
[52] U.S. Cl. ............... 564/48; 564/60; 564/147; 564/190; 564/201; 514/595; 514/596; 514/614
[58] Field of Search ............... 564/48, 60, 190, 564/201, 147; 514/595, 596, 614

[56] References Cited

U.S. PATENT DOCUMENTS

| | | | |
|---|---|---|---|
| 5,071,875 | 12/1991 | Horn et al. | 514/613 |
| 5,276,051 | 1/1994 | Lesieur et al. | 514/415 |

FOREIGN PATENT DOCUMENTS

| | | | |
|---|---|---|---|
| 48729/93 | 4/1994 | Australia | C07C 233/108 |
| WO94/07487 | 4/1994 | WIPO | A61K 31/40 |

OTHER PUBLICATIONS

Bernel et al., J. Agri. Food Chem., vol. 44, No. (10), pp. 3085–3089, 1996.
Burj et al., J. Amer. Chem. Soc. vol. 116, pp. 10847–10848, 1994.
Cullen et la., J. Chem. Soc. Perkin Trans I, vol. 20, pp. 2565–2579, 1995.
Tateba et al., Agric. Biol. Chem., vol. 55, No. 3, pp. 873–874, 1991.
Arendt, et al., "Alleviation of Jet Lag by Melatonin: Preliminary Results of Controlled Double Blind Trial", *British Medical Journal*, 292, p. 1170 (1986).
Cassone, et al., "Dose–Dependent Entrainment of Rat Circadian Rhythms by Daily Injection of Melatonin", *J. Biol. Rhythms,* 1, pp. 219–229, (1986).

Primary Examiner—S. Mark Clardy
Assistant Examiner—Sabiha N. Qazi
Attorney, Agent, or Firm—Aldo A. Algieri

[57] ABSTRACT

There is provided novel biphenylamido derivatives of the formula

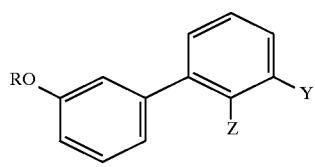

I wherein

Z is

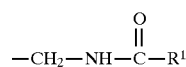

and Y is H or Z is H and Y is

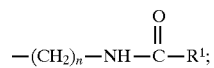

n is 0 or 1;

R is $C_{1-6}$ alkyl;

$R^1$ is $C_{1-3}$ alkyl, $C_{3-6}$ cycloalkyl, $C_{1-4}$ alkoxymethyl, or $NHR^2$; and $R^2$ is $C_{1-3}$ alkyl or cyclopropyl which are melatonergic agents and are useful in the treatment of circadian rhythm-related disorders and other conditions affected by melatonin activity.

9 Claims, No Drawings

BIPHENYLAMIDO DERIVATIVES AS MELATONERGIC AGENTS

CROSS-REFERENCE TO RELATED APPLICATION

This nonprovisional application claims the benefit of copending provisional application, U.S.S.N. 60/015,797 filed Apr. 17, 1996.

FIELD OF THE INVENTION

The present invention is directed to novel biphenylamido derivatives having drug and bio-affecting properties and to their preparation, pharmaceutical compositions thereof and methods of use. The compounds of the present invention possess melatonergic properties that are useful for the treatment of sleep and chronobiological disorders.

BACKGROUND OF THE INVENTION

Melatonin (N-acetyl-5-methoxytryptamine) is a hormone which is synthesized and secreted primarily by the pineal gland. In mammals, melatonin levels show a cyclical, circadian pattern, with highest levels occurring during the dark period of a circadian light-dark cycle. Melatonin is involved in the transduction of photoperiodic information and appears to modulate a variety of neural and endocrine functions in vertebrates, including the regulation of reproduction, body weight and metabolism in photoperiodic mammals, the control of circadian rhythms and the modulation of retinal physiology.

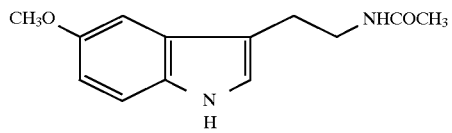

Melatonin

Recent evidence demonstrates that melatonin exerts its biological effects through specific receptors. Use of the biologically active, radiolabelled agonist [$^{125}$I]-2-iodomelatonin has led to the identification of high affinity melatonin receptors in the central nervous systems (CNS) of a variety of species. The sequence of one such high affinity melatonin receptor, cloned from frog melanocytes, has been reported. In mammalian brain, autoradiographic studies have localized the distribution of melatonin receptors to a few specific structures. Although there are significant differences in melatonin receptor distribution even between closely related species, in general the highest binding site density occurs in discrete nuclei of the hypothalamus. In humans, specific [$^{125}$I]-2-iodomelatonin binding within the hypothalamus is completely localized to the suprachiasmatic nucleus, strongly suggesting the melatonin receptors are located within the human biological clock.

Exogenous melatonin administration has been found to synchronize circadian rhythms in rats (Cassone, et al., J. Biol. Rhythms, 1:219–229, 1986). In humans, administration of melatonin has been used to treat jet-lag related sleep disturbances, considered to be caused by desynchronization of circadian rhythms (Arendt, et al., Br. Med. J. 292:1170, 1986). Further, the use of a single dose of melatonin to induce sleep in humans has been claimed by Wurtman in International Patent Application WO 94/07487, published on Apr. 14, 1994.

Melatonin binding sites have been found in several diverse tissues of the body, such as, in the retina, superchiasmatic nucleus and spleen. Since melatonin exerts multiple physiological effects, is not highly selective, and its potential for producing side effects is significant, there is a need for melatonin agonists which are more selective than melatonin and give fewer side effects.

In addition, melatonin's metabolic profile can be problematic in that the compound degrades rapidly in vivo and its oral bioavailability is often low and variable. Suitable melatonin agonists could overcome these drawbacks, resulting in products having more predictable activity.

Thus, melatonin agonists should be particularly useful for the treatment of sleep disorders and other chronobiological disorders. Melatonin agonists would also be useful for the further study of melatonin receptor interactions as well as in the treatment of conditions affected by melatonin activity, such as depression, work-shift syndrome, glaucoma, reproduction, cancer, immune disorders, neuroendorine disorders, and a variety of sleep disorders.

Aside from simple indole derivatives of melatonin itself, various amide structures have been prepared and their use as melatonin ligands disclosed. In general these amide structures can be represented by the general formula

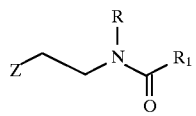

ii wherein Z is an aryl or heteroaryl system attached by a two carbon chain to the amide group. Some specific examples follow.

Lesieur, et al., in U.S. Pat. No. 5,276,051, issued Jan. 4, 1994, disclose as melatonin ligands arylethylamines 1,

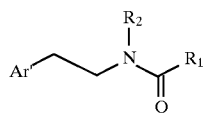

1 wherein Ar' is, inter alia, a substituted or unsubstituted benzo[b]thiophen-3-yl, benzimidazol-1-yl, benzo[b]furan-3-yl, 1,2-benzisoxazol-3-yl, 1,2-benzisothiazol-3-yl, or indazol-3-yl radical; $R_1$ is, inter alia, an alkyl or cycloalkyl group; and $R_2$ is hydrogen or lower alkyl.

Horn and Dubocovich in U.S. Pat. No. 5,071,875, issued Dec. 10, 1991, disclose 2-amidotetralins 2 as melatonin ligands,

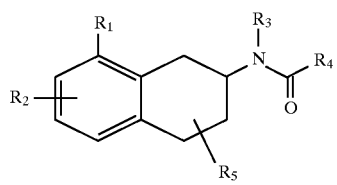

2 wherein $R_1$ is, inter alia, hydrogen, lower alkyl, or lower alkoxyl; $R_2$ is, inter alia, hydrogen, halogen, or lower alkoxyl; $R_3$ is, inter alia, hydrogen, or lower alkyl; $R_4$ is, inter alia, lower alkyl, haloalkyl or cycloalkyl; and $R_5$ is hydrogen, hydroxyl, halogen, oxo, aryl, lower alkyl or alkylaryl.

Langlois, et al., in Australian patent application AU-48729/93, published on Apr. 14, 1994, disclose arylalkyl(thio)amides 3 as melatonergic ligands,

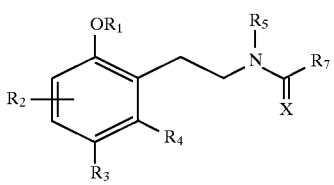

wherein $R_1$ is hydrogen or lower alkyl; $R_2$ is hydrogen, halogen, or lower alkyl; $R_3$ and $R_4$ are identical or different groups including, inter alia, hydrogen, halogen, or lower alkyl; $R_5$ is hydrogen or lower alkyl; X is sulfur or oxygen and $R_7$ is, inter alia, lower alkyl or alkenyl.

However these disclosures do not teach or suggest the novel melatonergic compounds of the present invention.

SUMMARY OF THE INVENTION

The present invention provides novel biphenylamido derivatives having the general formula

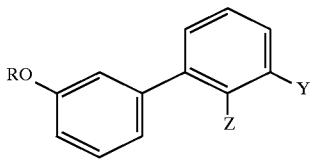

I wherein R, Z and Y are as defined below which are melatonergic agents. The present invention also provides pharmaceutical compositions comprising said biphenylamido derivatives and to the method of treatment of sleep and chronobiological disorders.

DETAILED DESCRIPTION OF THE INVENTION

The present invention provides novel biphenylamido derivatives which possess melatonergic properties and have the formula

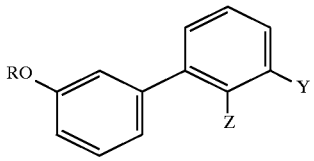

I wherein
Z is

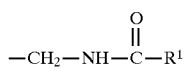

and Y is H or Z is H and Y is

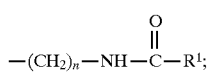

n is 0 or 1;
R is $C_{1-6}$ alkyl;
$R^1$ is $C_{1-3}$ alkyl, $C_{3-6}$ cycloalkyl, $C_{1-4}$ alkoxymethyl, or $NHR^2$; and
$R^2$ is $C_{1-3}$ alkyl or cyclopropyl.

The present invention also provides for the treatment of sleep and chronobiological disorders and other conditions affected by melatonin activity, which comprises administering alone or together with a conventional adjuvant, carrier or diluent a therapeutically effective amount of a compound of Formula I.

The terms "$C_{1-3}$ alkyl" and "$C_{1-6}$ alkyl" as used herein and in the claims (unless the context indicates otherwise) mean straight or branched chain alkyl groups such as methyl, ethyl, propyl, isopropyl, butyl, isobutyl, t-butyl, amyl, hexyl and the like. Preferably, these groups contain from 1 to 2 carbon atoms. The term "$C_{3-6}$ cycloalkyl" as used herein and in the claims means a carbon cyclic ring system such as cyclopropyl, cylobutyl, cyclopentyl and cyclohexyl. The term "$C_{1-4}$ alkoxymethyl" as used herein and in the claims means straight or branched chain alkoxymethyl groups such as methoxymethyl, ethoxymethyl, propoxymethyl, isopropoxymethyl, butoxymethyl and the like. Additionally, the compounds of Formula I also encompass all pharmaceutically acceptable solvates, hydrates being the preferred solvates.

In the method of the present invention, the term "therapeutically effective amount" means the total amount of each active component of the method that is sufficient to show a meaningful patient benefit, i.e., alleviating or ameliorating disorders associated with melatonin receptors. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims meaning alleviated or ameliorating circadian rhythm-related disorders such as sleep and chronobiological disorders and other conditions associated with melatonergic action.

In the compounds of Formula II, R is preferably methyl, $R^1$ is preferably propyl, cylcopropyl and $NHR^2$ wherein $R^2$ is preferably ethyl. In the compounds of Formula IIII, n is preferably 0 or 1, R is preferably ethyl, n-propyl, isopropyl, cyclopropyl, methoxymethyl and $NHR^2$ wherein $R^2$ is preferably ethyl.

The compounds of Formula I may be prepared by various procedures such as those illustrated herein in the examples, in the reaction schemes and variations thereof which would be evident to those skilled in the art. The various biphenylamido derivatives of Formula I may advantageously be prepared from substituted aryl halides which are generally well-known and a general method of preparation is illustrated in Reaction Schemes 1 and 2.

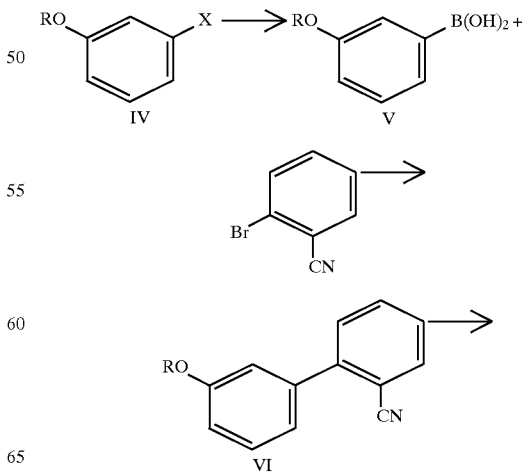

-continued
Reaction Scheme 1

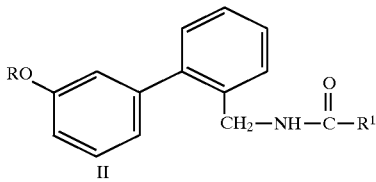

II

The preparation of substituted biphenyl compounds of Formula II is illustrated in Reaction Scheme 1. A suitable meta substituted alkoxy phenyl compound of Formula IV wherein X is chloro, bromo or iodo is treated with magnesium and the resulting Grignard solution is treated with trimethylborate and hydrolyzed to produce the substituted phenylboronic acid of Formula V. The compound of Formula V is readily cross-coupled to various cyanoarylbromides under Suzuki condition as generally described by A. R. Martin and Y. Yang in *Acta. Chem. Scand.*, 47, 221–230 (1993) to generate the cyanobiphenyl compounds of Formula VI. The cyano group of the biphenyl compound of Formula VI is readily reduced with reducing agents which are generally known, such as with lithium aluminum hydride to produce the intermediate benzyl amine which is then acylated with acid chlorides or isocyanates to produce the compounds of Formula II by standard procedures well-known to those skilled in the art.

The preparation of biphenyl compounds of Formula III wherein n=0 or 1 is illustrated in Reaction Scheme 2 for the compounds of Formula IIIa and IIIb. The phenylboronic acid of Formula V is cross-coupled to either nitroaryl or cyanoaryl bromides under Suzuki conditions to nitrobiphenyl compounds of Formula VII or cyanobiphenyl compounds of Formula VIII. When it is desired to prepare the biphenyl compounds of Formula IIIa, the nitro group of the corresponding compound of Formula VII is first reduced by methods well-known in the art, such as hydrogenation with hydrogen and sulfided platinum as a catalyst to generate the intermediate anilines. Subsequent acylation of the anilines with acid chlorides or isocyanates will produce the amides or ureas of the compounds of Formula IIIa. When it is desired to prepare the biphenyl compounds of Formula IIIb, the cyano group of the corresponding compound of Formula VIII is first reduced with a reducing agent such as lithium aluminum hydride in an inert organic solvent such as tetrahydrofuran and the like to generate the aminomethyl intermediates. Subsequent acylation of the amine with acid chlorides or isocyanates will produce the amides or ureas of the compounds of Formula IIIb.

In a preferred embodiment of the invention the compounds of Formula II have the formula

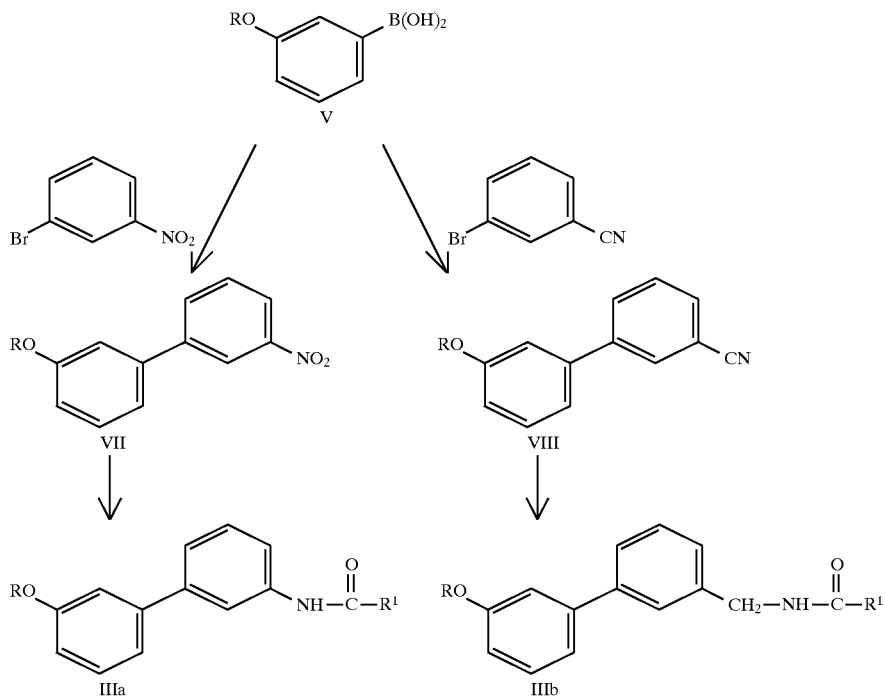

II

[Structure: biphenyl with RO- on one ring and -CH₂-NH-C(=O)-R¹ on the other]

wherein R is methyl, $R^1$ is n-propyl, isopropyl, cyclopropyl or $NHR^2$ and $R^2$ is ethyl.

In another preferred embodiment of the invention the compounds of Formula III have the formula

III

[Structure: biphenyl with RO- on one ring and -(CH₂)ₙ-NH-C(=O)-R¹ on the other]

wherein R is methyl, n is 0 or 1 and $R^1$ is ethyl, n-propyl, isopropyl or cyclopropyl.

In another aspect, this invention provides a method for the treatment or alleviation of disorders associated with melatonin activity in a mammal in need thereof, which comprises administering to said mammal a therapeutically effective amount of a compound of Formula I. Preferably, the compounds of Formula I are useful in the treatment of sleep and chronobiological disorders.

In still another aspect, this invention provides pharmaceutical compositions comprising at least one compound of Formula I in combination with a pharmaceutical adjuvant, carrier or diluent.

MEASUREMENT OF MELATONERGIC BINDING

The melatonergic binding of the compounds of Formula I was determined by the method of Reppert, S. M., et al., as described in Neuron, Vol. 13, 1177–1185 (1994) and Proc. Nat. Acad. Sci. USA, 92, 8734–8738 (1995) and also as described by Stankov, B., et al., "Characterization and mapping of melatonin receptors in the brain of three mammalian species: Rabbit, horse and sheep," in Neuroendocrinology, 53, 214–221 (1991). The assays were incubated at 37° C. for 1 hour, and the reaction was terminated by filtration through a Brandel cell harvester. The filters were washed 3 times with wash buffer. Compounds with $IC_{50}$ values less than 250 nM are preferred, while compounds with $IC_{50}$ values less than 50 nM are more preferred. The reagents, membranes, and techniques used in the melatonergic binding assays are more fully described below:

1. Reagents
   (a) 50 mM Tris buffer containing 12.5 mM $MgCl_2$ and 2 mM EDTA (pH 7.4 at 37° C.).
   (b) Wash buffer: 20 mM Tris base containing 2 mM $MgCl_2$ (pH 7.4 at room temperature).
   (c) 6-Chloromelatonin ($10^{-5}$M final concn.).
   (d) 2-[$^{125}$I]-Iodomelatonin. Source: New England Nuclear 2. Tissue Preparation for $ML_1$ Binding Male New Zealand white rabbits (Hazelton Research) are decapitated, the brains are rapidly removed and chilled. The parietal cortex is crudely dissected and the tissue frozen on dry ice at −80° C. until assayed. Tissue is weighed and thawed in 20 mls of ice-cold Tris buffer (a) and then homogenized by treatment with a polytron for 10 seconds at setting 17. Ice cold Tris (a) is added to a volume of 40 ml. The homogenate is centrifuged in a Sorvall-SS-34 head at 19,000 rpm (44,000× g) for 20 min at 4° C. The resulting supernatant is decanted and discarded. The pellet is re-homogenized in an additional 20 ml of Tris buffer, diluted and centrifuged as before. The supernatant is decanted and discarded. The resulting pellet is homogenized in 20 volumes of Tris buffer per gram of original tissue (a 1:20 homogenate), chilled, and held on ice until assayed.

3. Membrane preparation for $ML_{1a}$ Binding.

The cDNA (human $ML_{1a}$) was introduced into COS-1 cells by the DEAE-dextran method. Three days later, the media was removed, the plates washed with phosphate buffered saline, the cells removed using Hank's balanced salt solution and pelleted. The supernatant was discarded and the pellets frozen. For preparing membrane homogenates, the pellets are thawed on ice, and resuspended in TME buffer [Tris base, $MgCl_2$, EDTA (pH 7.4 at 37° C.], supplemented with aprotinin, leupeptin and phenylmethylsulfonylfluoride. The cells were then homogenized using a dounce homogenizer and centrifuged. The resulting pellet was resuspended with a dounce homogenizer in TME and frozen. On the day of assay, a small aliquot was thawed on ice and resuspended in TME buffer (1:1000).

Reasonable variations, such as those which would occur to a skilled artisan, can be made herein without departing from the scope of the invention.

TABLE I

| Example | In-Vitro Receptor Binding Activities $ML_1$ $(IC_{50})^a$ |
|---|---|
| 1 | +++ |
| 2 | + |
| 3 | $NT^b$ |
| 4 | NT |
| 5 | NT |
| 6 | + |
| 7 | ++ |
| 8 | +++ |
| 9 | +++ |
| 10 | ++ |
| 11 | +++ |
| 12 | ++ |

$^a$ = $IC_{50}$ values for $ML_1$ rabbit melatonin receptor binding
+++ = <10 nM
++ = 10–50 nM
+ = >50 nM
$^b$NT = not tested

TABLE II

| Example | In-Vitro Receptor Binding Activities $ML_{1a}$ $(IC_{50})^b$ |
|---|---|
| 1 | A |
| 2 | A |
| 3 | A |
| 4 | A |
| 5 | C |
| 6 | C |
| 7 | B |
| 8 | B |
| 9 | B |
| 10 | C |
| 11 | B |
| 12 | C |

$^b$ = $IC_{50}$ values for $ML_{1a}$ human melatonin receptor binding
A = <100 nM
B = 100–300 nM
C = >300 nM The compounds of the present invention have affinity for receptors of the endogenous pineal hormone, melatonin, as determined in a receptor binding assays, as described above in Tables 1 and 2 for the $ML_1$ (rabbit) and $ML_{1a}$ (human) receptors, respectively. Melatonin is involved in the regulation of a variety of biological rhythms and exerts its biological effects via interaction with specific receptors. There is evidence that administration of melatonin agonists are of clinical utility in the treatments of various conditions regulated by melatonin activity. Such conditions include depression, jet-lag, work-shift syndrome, sleep disorders, glaucoma, and some disorders associated with reproduction, cancer, immune disorders and neuroendocrine disorders.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

The pharmaceutical compositions include suitable dosage forms for oral, parenteral (including subcutaneous, intramuscular, intradermal and intravenous) transdermal, bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Particularly useful is the administration of a compound of Formula I in oral dosage formulations. The pharmaceutical compositions are prepared by conventional techniques appropriate to the desired preparation containing appropriate amounts of the active ingredient, that is, the compound of Formula I according to the invention. See, for example, *Remington's Pharmaceutical Sciences*, Mack Publishing Company, Easton, Pa., 17th edition, 1985.

The dosage of the compounds of Formula I to achieve a therapeutic effect will depend not only on such factors as the age, weight and sex of the patient and mode of administration, but also on the degree of melatonergic activity desired and the potency of the particular compound being utilized for the particular disorder or condition concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

A suitable dose of a compound of Formula I or pharmaceutical composition thereof for a mammal, including man, suffering from, or likely to suffer from any condition as described herein is an amount of active ingredient from about 0.1 mg to about 100 mg per day. The active ingredient will preferably be administered in equal doses from one to four times a day. However, usually a small dosage is administered, and the dosage is gradually increased until the optimal dosage for the host under treatment is determined.

However, it will be understood that the amount of the compound actually administered will be determined by a physician, in the light of the relevant circumstances including the condition to be treated, the choice of compound of be administered, the chosen route of administration, the age, weight, and response of the individual patient, and the severity of the patient's symptoms.

The following examples are given by way of illustration and are not to be construed as limiting the invention in any way inasmuch as many variations of the invention are possible within the spirit of the invention.

DESCRIPTION OF SPECIFIC EMBODIMENTS

In the following examples, all temperatures are given in degrees Centigrade. Melting points were recorded on a capillary melting point apparatus and the temperatures are uncorrected. Proton magnetic resonance ($^1$H NMR) spectra were recorded on a Bruker AC 300 spectrometer. All spectra were determined in the solvents indicated and chemical shifts are reported in δ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; dd, doublet of doublet; bd, broad doublet; dt, doublet of triplet; bs, broad singlet; dq, doublet of quartet. Infrared (IR) spectra are reported in reciprocal centimeters ($cm^{-1}$). The element analysis are reported as percent by weight.

Preparation No. 1

3-Methoxyphenylboronic Acid

Magnesium turnings (10.4 g, 428 mmol) were placed in a three-necked flask equipped with one condenser and one addition funnel and the flask was flame-dried under a stream of nitrogen. Rubber septa were used to enclose the vessel and the reaction was run under a stream of nitrogen. A solution of 3-bromoanisole (40 g, 214 mmol) in THF (400 mL) was placed in the addition funnel. The magnesium turnings were covered with THF and warmed to 65° C. A crystal of iodine and then a few mL of the anisole solution were added to the turnings. A few minutes later the amber color disappeared. The anisole solution was then slowly dripped into the reaction vessel. After all of the anisole was added, the reaction was maintained at 65° C. for 2 h. After cooling to ambient temperature, the Grignard solution was poured into a solution of trimethylborate (24.96 g, 240 mmol) in diethylether (250 mL) and stirred for 1 h. The solution was quenched with 1N HCl and extracted with ether. The ether was removed by rotary evaporation leaving the boronic acid as an white solid (27.59 g, 181.51 mmol).

$^1$H NMR (CDCl$_3$) δ7.38–7.33 (m, 2H), 7.24 (t, J=7.8 Hz, 1H), 6.95 (dd, J=7.8, 2.7 Hz, 1 H), 3.74 (s, 3H); $^{13}$C NMR (CDCl$_3$) δ158.6, 158.5, 128.5, 126.3, 119.0, 115.7, 54.8. Anal. Calcd for C$_7$H$_9$BO$_3$: C, 55.33; H, 5.97.Found: C, 55.48; H, 5.89.

Preparation No. 2

General Procedure for Cross-coupling Boronic Acid of Formula V with Aryl Bromides Aryl boronic acid of Formula V (1 equiv), aryl bromide (1 equiv), and tetrakistriphenylphosphine palladium (0.5 mol %) were refluxed in a 1:1 solution of benzene and 2N aqueous sodium carbonate (ca. 0.25M) until TLC indicated the reaction was complete (generally at least 16 h). The reaction mixture was cooled and the aqueous layer decanted and washed with methylene chloride. The combined organic layers were dried and filtered and the solvent removed by rotary evaporation. The crude yield was usually near quantitative and the crude reaction product was taken directly to the next synthetic step.

Preparation No. 3

General Procedure for Hydrogenation of Nitro Compounds of Formula VII

The nitro compound was taken up in ethyl acetate and sulfided platinum catalyst (5–10 wt %) added under nitrogen. The reaction mixture was then hydrogenated on a Parr shaker at 50 psi until the TLC indicated the completion of the reduction (generally at least 12 h). The solution was filtered and the solvent removed by rotary evaporation to generate the crude amine. Yields were generally near quantitative and the amine was directly taken to the next synthetic step.

Preparation No. 4

General Procedure for Reduction of Cyano Compounds of Formulas VI and VIII

Lithium aluminum hydride (1 mol equiv) was suspended in THF (ca. 0.5M) at 0° C. and a solution of the cyano compound (1 equiv) in THF was slowly added through an addition funnel. The reaction was stirred until TLC indicated the reduction was complete (generally 2 h). Ether was added and the reaction quenched by slowly adding water dropwise (1g/mmol LAH) followed by 15% NaOH (1g/mmol LAH) and more water (3g/mmol LAH). The reaction was then stirred for 30–60 min before filtering the solution. The solvent was removed by rotary evaporation generating the crude amine. The crude yield was generally 80–100% and the amine was directly taken to the next synthetic step.

Preparation No. 5

General Procedure for Preparation of Amides of Formulas II, IIIa and IIIb

The appropriate acyl chloride (1 equiv) was dissolved in methylene chloride and a solution of the amine (1 equiv) and 4-dimethyl-aminopyridine (1 equiv) in methylene chloride (ca. 0.5M) were slowly added through an addition funnel. The reaction was stirred at ambient temperature until the TLC indicated the reaction was complete (generally 2 h). The reaction was quenched with 1N HCl and the organic layer separated. The aqueous layer was washed with methylene chloride and the combined organic layers were dried and the solvent removed by rotary evaporation. The crude amides were purified by flash chromatography (generally 25% ethyl acetate/hexane) to generate the pure amides in 85–95% yield.

Preparation No. 6

General Procedure for Preparation of Ethyl Ureas of Formulas II, IIIa and IIIb

Ethyl isocyanate was dissolved in THF (ca. 0.5M) and a solution of the amine (1 equiv) and 4-dimethylaminopyridine (1 equiv) in THF were slowly added through an addition funnel. The reaction was stirred at ambient temperature until the TLC indicated the reaction was complete (generally 2 h for benzyl amines and at least 12 h for anilines). The reaction was quenched with 1N HCl and the organic layer separated. The aqueous layer was washed with methylene chloride and the combined organic layers were dried and the solvent removed by rotary evaporation. The crude ureas were purified by flash chromatography (generally 25–50% ethyl acetate/hexane) to generate the pure ureas in 80–100% yield (anilines gave the lower yields).

EXAMPLE 1

N-(3'-Methoxy-[1,1'-biphenyl]-3-yl)butanamide mp 90°–91° C. IR 1664 cm$^{-1}$; $^1$H NMR (CDCl$_3$) δ 0.98 (t, J=6.0 , 3H), 1.75 (sex, J=6.0, 2H), 2.33 (t, J=6.0, 2H), 3.82 (s, 3H), 6.86 (dd, J=9.0, 2.1, 1H), 7.08 (t, J=1.8, 1H), 7.13 (d, J=7.5, 1H), 7.33 (m, 3H), 7.50 (d, J=7.5, 1H), 7.72 (s, 1H); $^{13}$C NMR (CDCl$_3$) δ 13.8, 19.0, 39.7, 55.3, 112.8, 113.0, 118.6, 118.9, 119.7, 123.0, 129.3, 129.7, 138.3, 141.9, 142.2, 159.9, 171.4. Anal. Calcd for C$_{17}$H$_{19}$NO$_2$. 0.18 H$_2$O: C, 74.91; H, 7.16; N, 5.14. Found: C, 74.92; H, 7.20; N, 5.12.

EXAMPLE 2

N-(3'-Methoxy-[1,1'-biphenyl]-3-yl)2-methylpropanamide mp 112°–114° C.; IR 1660 cm$^{-1}$; $^1$H NMR (CDCl$_3$) δ 1.25 (d, J=6.9, 6H), 2.51 (hep, J=6.9, 1H), 3.83 (s, 3H), 6.86 (dd, J=8.4, 2.3, 1H), 7.09 (t, J=1.8, 1H), 7.15 (d, J=7.5, 1H), 7.33 (m, 3H), 7.50 (d, J=7.8, 1H), 7.75 (s, 1H); $^{13}$C NMR (CDCl$_3$) δ 19.6, 36.8, 55.3, 112.8, 113.0, 118.6, 118.7, 119.7, 123.0, 129.3, 129.7, 138.4, 142.0, 142.2, 159.9, 175.3. Anal. Calcd for C$_{17}$H$_{19}$N$_1$O$_2$: C, 75.81; H, 7.11; N, 5.20. Found: C, 75.75; H, 7.19; N, 5.11.

EXAMPLE 3

N-(3'-Methoxy-[1,1'-biphenyl]-3-yl) cyclopropanecarboxamide mp 150°–152° C.; IR 1656 cm$^{-1}$; $^1$H NMR (CDCl$_3$) δ 0.61 (m, 2H), 0.85 (m, 2H), 1.55 (m, 1H), 3.65 (s, 3H), 6.67 (d, J=8.1,1H), 6.97 (s, 1H), 6.98 (d, J=7.8, 1H), 7.13 (m, 3H), 7.37 (d, J=7.5, 1H), 7.71 (s, 1H); $^{13}$C NMR (CDCl$_3$) δ 7.6, 14.9, 55.1, 112.6, 118.3, 118.4, 119.4, 122.1, 126.9, 129.0, 129.6, 139.2, 141.4, 142.3, 159.7, 172.6. Anal. Calcd for C$_{17}$H$_{17}$NO$_2$: C, 76.38; H, 6.41; N, 5.24. Found: C, 76.17; H, 6.54; N, 5.21.

EXAMPLE 4

N-(3'-Methoxy-[1,1 '-biphenyl]-3-yl)propanamide mp 117°–119° C.; IR 1668 cm$^{-1}$; $^1$H NMR (CDCl$_3$) δ 1.21 (t, J=7.5, 3H), 3.37 (q, J=7.5, 2H), 3.81 (s, 3H), 6.86 (d, J=8.1, 1H), 7.08 (s, 1H), 7.12 (d, J=7.8,1H), 7.29 (m , 3H), 7.51 (d, J=7.2,1H), 7.73 (d, J=6.6, 1H); $^{13}$C NMR (CDCl$_3$) δ 9.7, 30.7, 55.3, 112.8, 112.9, 118.2, 119.0, 119.7, 123.0, 129.3, 129.7, 138.5, 141.9, 142.2, 159.9, 172.5. Anal. Calcd for C$_{16}$H$_{17}$NO$_2$: C, 75.27; H, 6.71; N, 5.49. Found: C, 75.21; H, 6.72; N, 5.46.

EXAMPLE 5

N-(3'-Methoxy-[1,1'-biphenyl]-3-yl)-2-methoxyacetamide

IR 1684 cm$^{-1}$; $^1$H NMR (CDCl$_3$) δ 3.49 (s, 3H), 3.84 (s, 3H), 4.01 (s, 2H), 6.88 (d, J=8.4, 1H), 7.10 (s, 1H), 7.16 (d,

J=7.8, 1H), 7.35 (m, 3H), 7.60 (d, J=7.50, 1H), 7.76 (s, 1H), 8.34 (bs, 1H); $^{13}$C NMR (CDCl$_3$) δ 55.3, 59.3, 72.1, 112.8, 113.0, 118.5, 118.8, 119.7, 123.4, 129.4, 129.7, 137.6, 142.0, 142.1, 159.9, 167.6. Anal. Calcd for C$_{16}$H$_{17}$NO$_3$:C, 70.83; H, 6.32; N, 5.16. Found: C, 70.52; H, 6.21; N, 4.87.

EXAMPLE 6

N-Ethyl N'-(3'-methoxy-[1,1'-biphenyl]-3-yl)urea mp 152°–154° C.; IR 1650 cm$^{-1}$; $^1$H NMR (CDCl$_3$) δ 1.39 (t, J=7.2, 3H), 3.29 (q, J=7.2, 2H), 6.87 (d, J=8.1, 1H), 7.06 (s, 1H), 7.08 (d, J=7.5, 1H), 7.32 (m, 4H), 7.47 (s 1H). Anal. Calcd for C$_{16}$H$_{18}$N$_2$O$_2$. 0.17 H$_2$O: C, 70.32; H, 6.76; N, 10.25. Found: C, 70.28; H, 6.43; N, 10.53.

EXAMPLE 7

N-[(3'-Methoxy[1,1'-biphenyl]-2-yl)methyl]butanamide mp 55°–57° C.; IR 1626 cm$^{-1}$; $^1$H NMR (CDCl$_3$) δ 0.86 (t, J=7.5, 3H), 1.57 (sex, J=7.5, 2H), 2.05 (t, J=7.5, 2H), 3.79 (s, 3H), 4.38 (d, J=5.7, 2H), 5.60 (bs, 1H), 6.81 (m, 3H), 7.31 (m 5H); $^{13}$C NMR (CDCl$_3$) δ 13.8, 19.1, 38.6, 41.4, 43.5, 55.3, 112.8, 114.7, 121.4, 127.4, 127.8, 129.4, 130.0, 135.6, 141.5, 142.1, 159.5, 172.6. Anal. Calcd for C$_{18}$H$_{21}$NO$_2$. 0.10H$_2$O: C, 75.79; H, 7.50; N, 4.91. Found: C, 75.81; H, 7.53; N, 4.78.

EXAMPLE 8

N-[(3'-Methoxy[1,1'-biphenyl]-2-yl)methyl]-2-methylpropanamide mp 103°–105° C.; IR 1626 cm$^{-1}$; $^1$H NMR (CDCl$_3$) δ 1.05 (d, J=7.0, 6H), 2.24 (hep, J=7.0, 1H), 3.80 (s, 3H), 4.40 (d, J=6.0, 2H), 5.48 (bs, 1H), 6.87 (m, 3H), 7.30 (m, 5H); $^{13}$C NMR (CDCl$_3$) δ 19.5, 35.6, 41.5, 112.8, 114.6, 121.4, 127.4, 127.8, 128.8, 129.4, 130.1, 135.6, 141.5, 142.1, 159.5, 176.4. Anal. Calcd for C$_{18}$H$_{21}$NO$_2$. 0.20 H$_2$O: C, 75.36; H, 7.52; N, 4.88. Found: C, 75.35; H, 7.36; N, 4.92.

EXAMPLE 9

N-Ethyl N'-[(3'-methoxy[1,1'-biphenyl]-2-yl)methyl]urea mp 110°–112° C.; IR 1618 cm$^{-1}$; $^1$H NMR (CDCl$_3$) δ 1.02 (t, J=9.0, 3H), 3.05 (bm, 2H), 3.79 (s, 3H), 4.26 (d, J=6.0, 2H), 4.42 (bs, 1H), 4.67 (bm, 1H), 6.85 (m, 3H), 7.26 (m, 4H), 7.41 (m, 1H); 13C NMR (CDCl$_3$) δ 15.4, 35.3, 42.3, 55.2, 112.8, 114.7, 121.5, 127.1, 127.8, 128.4, 128.6, 129.9, 136.5, 141.3, 142.2, 158.0, 159.4. Anal. Calcd for C$_{17}$H$_{20}$N$_2$O$_2$: C, 71.81; H, 7.09; N, 9.85. Found: C, 71.45; H, 7.01; N, 9.54.

EXAMPLE 10

N-[(3'-methoxy-[1,1'-biphenyl]-3-yl)methyl]butanamide

IR 1644 cm$^{-1}$; $^1$H NMR (CDCl$_3$) δ 0.94 (t, J=7.2, 3H), 1.67 (sex, J=7.5, 2H), 2.18 (t, J=7.8, 2H) 3.84 (s, 3H), 4.48 (d, J=5.4, 2H), 5.75 (bs, 1H), 6.87 (d, J=8.1, 1H), 7.07 (s, 1H), 7.13 (d, J=7.8, 1H), 7.24 (d, J=7.5, 1H), 7.34 (m, 2H), 7.47 (m, 2H); $^{13}$C NMR (CDCl$_3$) δ 13.8, 19.2, 38.7, 43.6, 55.3, 112.9, 112.9, 119.7, 126.4, 126.7, 126.9, 129.1, 129.8, 138.9, 141.6, 142.3, 160.0, 172.8. Anal. Calcd for C$_{18}$H$_{21}$NO$_2$. 0.16 H$_2$O: C, 75.53; H, 7.51; N, 4.89. Found: C, 75.55; H, 7.68; N, 5.02.

EXAMPLE 11

N-[(3'-methoxy-[1,1'-biphenyl]-3-yl)methyl]-2-methylpropanamide 1648 cm$^{-1}$; $^1$H NMR (CDCl$_3$) δ 1.15 (d, J=6.9, 6H), 2.38 (hep, J=6.9, 1H), 3.82 (s, 3H), 4.44 (d, J=5.7, 2H), 6.03 (bs, 1H), 6.87 (d, J=8.4, 1H), 7.07 (s, 1H), 7.12 (d, J=7.5, 1H), 7.21 (d, J=7.5, 1H), 7.30 (m, 2H), 7.45 (m, 2H); $^{13}$C NMR (CDCl$_3$) δ 19.7, 35.6, 43.4, 55.3, 112.8, 112.9, 119.6, 126.3, 126.5, 126.7, 129.1, 129.8, 139.1, 141.51, 142.4, 160.0, 176.9. Anal. Calcd for C$_{18}$H$_{21}$NO$_2$. 0.16 H$_2$O: C, 75.50; H, 7.51; N, 4.89.

Found: C, 75.48; H, 7.19; N, 4.98.

EXAMPLE 12

N-Ethyl N'-[(3'-methoxy-[1,1'-biphenyl]-3-yl)methyl]urea

IR 1624 cm$^{-1}$; $^1$H NMR (CDCl$_3$) δ 0.97 (d, J=7.2, 3H), 3.05 (q, J=7.2, 2H), 3.80 (s, 3H), 4.26 (d, J=5.7, 2H), 5.18 (bs, 1H), 5.56 (bs, 1H), 6.84 (d, J=8.4,1H), 7.03 (s, 1H), 7.07 (d, J=7.5, 1H), 7.15 (d, J=6.0, 1H), 7.29 (m, 2H), 7.38 (m, 2H); $^{13}$C NMR (CDCl$_3$) δ 15.4, 35.1, 44.2, 55.3, 112.7, 112.9, 119.6, 125.9, 126.1, 126.4, 128.9, 129.7, 140.1, 141.26, 142.5, 158.7, 159.7. Anal. Calcd for C$_{17}$H$_{20}$N$_2$O$_2$. 0.33H$_2$O: C, 70.34; H, 7.17; N, 9.65. Found: C, 70.31; H, 7.11; N, 9.67.

We claim:

1. A compound of the formula

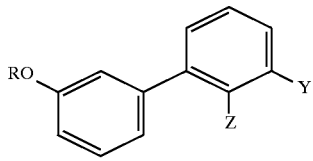

wherein

Z is

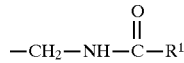

and

Y is H or Z is H and Y is

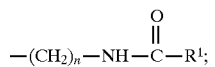

n is 0 or 1;

R is C$_{1-6}$ alkyl;

R$^1$ is C$_{1-3}$ alkyl, C$_{3-6}$ cycloalkyl, C$_{1-4}$ alkoxymethyl, or NHR$^2$; and R$^2$ is C$_{1-3}$ alkyl or cyclopropyl.

2. A compound of claim 1 having the formula

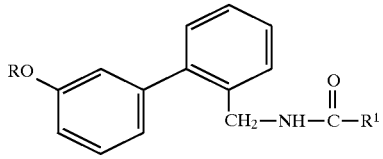

wherein

R is C$_{1-6}$ alkyl;

R$^1$ is C$_{1-3}$ alkyl, C$_{3-6}$ cycloalkyl, C$_{1-4}$ alkoxymethyl, or NHR$^2$; and R$^2$ is C$_{1-3}$ alkyl or cyclopropyl.

3. A compound of claim 1 having the formula

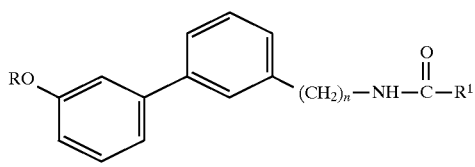

III wherein

R is $C_{1-6}$ alkyl;

n is 0 or 1;

$R^1$ is $C_{1-3}$ alkyl, $C_{3-6}$ cycloalkyl, $C_{1-4}$ alkoxymethyl, or $NHR^2$; and $R^2$ is $C_{1-3}$ alkyl or cyclopropyl.

4. A compound of claim 1 wherein R is methyl.

5. A compound of claim 2 wherein R is methyl, $R^1$ is n-propyl, isopropyl or $NHR^2$ and $R^2$ is ethyl.

6. A compound of claim 3 wherein R is methyl, n is 0 or 1 and $R^1$ is ethyl, n-propyl, isopropyl or cyclopropyl.

7. The compound of claim 1 which is N-(3'-methoxy-[1,1'-biphenyl]-3-yl)butanamide.

8. A method of treating a circadian rhythm-related disorder in a patient in need of such treatment, which comprises administering to said patient a therapeutically effective amount of a compound of claim 1.

9. A pharmaceutical composition for treating circadian rhythm-related disorders comprising a therapeutically effective amount of a compound of claim 1 and a suitable amount of a pharmaceutically acceptable carrier or diluent.

* * * * *